United States Patent
Katcha et al.

(10) Patent No.: US 7,079,619 B2
(45) Date of Patent: Jul. 18, 2006

(54) SYSTEM AND METHOD FOR DATA SLIPRING CONNECTION

(75) Inventors: Jason Stuart Katcha, Whitefish Bay, WI (US); Nathanael Dale Huffman, Mishawaka, IN (US); James K. Omick, New Berlin, WI (US); Phil E. Pearson, Jr., Hartland, WI (US)

(73) Assignee: GE Medical Systems Global Technology Company, LLC., Waukesha, WI (US)

( * ) Notice: Subject to any disclaimer, the term of this patent is extended or adjusted under 35 U.S.C. 154(b) by 228 days.

(21) Appl. No.: 10/707,478

(22) Filed: Dec. 17, 2003

(65) Prior Publication Data

US 2005/0135551 A1    Jun. 23, 2005

(51) Int. Cl.
*H05G 1/60* (2006.01)

(52) U.S. Cl. ............................................. 378/15; 378/4

(58) Field of Classification Search ............... 378/4–20
See application file for complete search history.

(56) References Cited

U.S. PATENT DOCUMENTS

| | | | |
|---|---|---|---|
| 5,530,425 A | 6/1996 | Harrison | 340/500 |
| 6,301,324 B1 | 10/2001 | Pearson, Jr. et al. | 378/15 |
| 6,433,631 B1 | 8/2002 | Pearson, Jr. et al. | 329/311 |
| 6,641,429 B1 | 11/2003 | Wu | 439/465 |

*Primary Examiner*—Edward J. Glick
*Assistant Examiner*—Jurie Yun
(74) *Attorney, Agent, or Firm*—Cantor Colburn LLP (57) ABSTRACT

A direct electrical connection is provided between transmission line segments of a data slipring and a data acquisition system. A transformer may be provided between the data acquisition system and the transmission line segments for correcting an impedance mismatch between the slipring and the electrical connection. A method of connecting the data slipring with the data acquisition system includes providing a controlled impedance electrical cable between the transmission line segments and the data acquisition system.

29 Claims, 7 Drawing Sheets

CT Data Slipring with Direct Electrical Connection

CT Data Slipring with Direct Electrical Connection

FIG. 7

SYSTEM AND METHOD FOR DATA SLIPRING CONNECTION

BACKGROUND OF INVENTION

Field of the Invention

This invention relates generally to a data slipring for a computerized tomography ("CT") scanner, and more particularly, this invention relates to an improved connection between a data acquisition system ("DAS") and the slipring.

CT systems are used to obtain non-invasive sectional images of test objects, particularly internal images of human tissue for medical analysis and treatment. Current CT systems position the test object, such as a patient, on a table within a central aperture of a rotating frame, or gantry, which is supported by a stationary frame. The gantry includes an x-ray source and a detector array positioned on opposite sides of the aperture, within an x-y plane of a Cartesian coordinate system (generally referred to as the "imaging plane"), such that both rotate with the gantry around the test object being imaged. At each of several angular positions along the rotational path of the gantry (also referred to as "projections"), the x-ray source emits a fan-shaped collimated beam which passes through the imaging slice of the test object, is attenuated by the test object, and is received by the detector array. Each detector element in the detector array produces a separate electrical signal indicative of the attenuated x-ray beam intensity, the beam projected from the x-ray source to the particular detector element, incident at its sensor surface. The electrical signals from all the detector elements are collated by circuitry within the rotating frame to produce a projection data set at each gantry angle or projection. Each projection data set is referred to as a "view", and a "scan" is a set of such views from the different gantry angles during one revolution of the x-ray source and detector array. The scan is then processed by a computer in the stationary frame to reconstruct the projection data sets into a CT image of the slice or cross-section of the test object.

To transfer the projection data sets from the rotating frame to the stationary frame for image reconstruction, various communication links such as an umbilical cable, an optical data link, a slipring with a contacting brush, and a slipring with a contactless coupler are currently available. Newer CT systems typically utilize a slipring disposed on the rotating frame with a contactless coupler, having a certain air gap with respect to the slipring, disposed on the stationary frame as the communication link between the rotating and stationary frames. The slipring comprises a broken circle of wire or transmission line encircling the aperture of the rotating frame such that each half of the broken circle of wire forms an arc of exactly the same length. Data signals, e.g., the projection data sets, are encoded and transmitted from the first ends of the two wires to the second ends of the two wires at the opposite side of the broken circle such that both data signals arrive at the second ends, generally referred to as the termination gap, at the same time. The contactless coupler disposed on the stationary frame lies close to the slipring and captures the transmitted encoded data signals via electromagnetic coupling. Because each projection data set is transmitted as they are acquired (after encoding), i.e., while the rotating frame is still rotating to acquire the next projection data set for the next gantry angle, propagation of the data signals along the wires of the slipring and electromagnetic coupling from the slipring to the contactless coupler occurs while the rotating frame and thus the slipring are in rotation.

Figure 1:
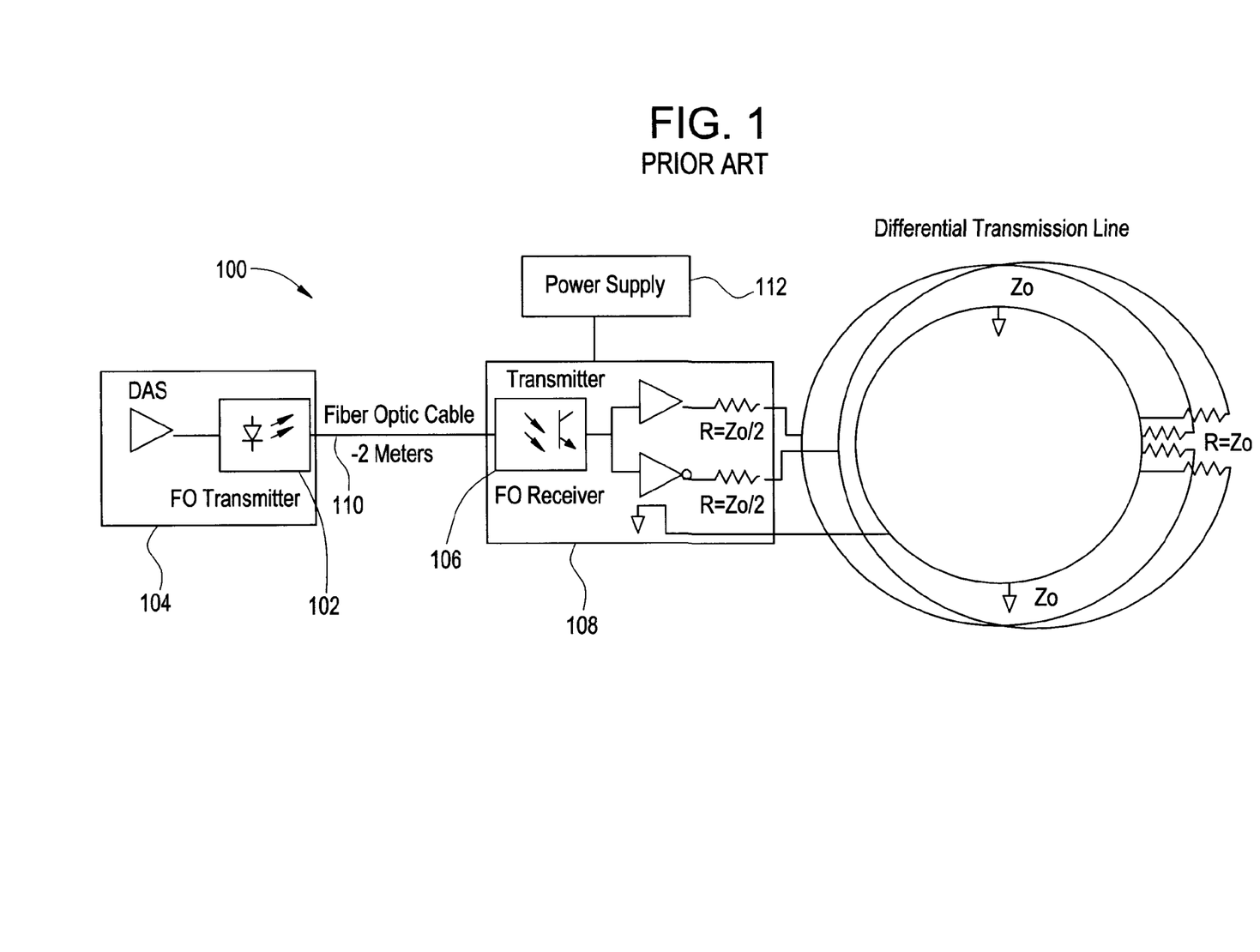
FIG. 1 shows a schematic block diagram of a portion of a prior art CT system.

As shown in FIG. 1, a prior art system 100 sends the high speed data from the slipring and converts it to an optical signal by electronics, the electronics including a fiber optic transmitter 102 in the data acquisition system 104 and the fiber optic receiver 106 in the transmitter 108, connected by a fiber optic cable 110, and a power supply 112 to power the transmitter 108. The use of optical technologies allows for fast data transfer without introducing unnecessary noise, which can be problematic as the data speeds continue to increase past 1 GHz. Optical fibers are also a common choice because they are relatively inexpensive, can be drawn to small diameters, are lightweight and non-flammable, and provide very little signal degradation. The optical approach, however, requires complicated electronics 102, 106 and a separate power supply 112 to convert the electrical signal to an optical one, adding complexity and cost to the system 100.

SUMMARY OF INVENTION

The above discussed and other drawbacks and deficiencies of the prior art are overcome or alleviated by a system for image reconstruction having a data slipring including transmission line segments, a data acquisition system, and a direct electrical connection between the transmission line segments and the data acquisition system.

In another exemplary embodiment of the invention, a system for image reconstruction includes a data slipring having transmission line segments, a data acquisition system, a transformer, and an electrical connection between the transmission line segments and the data acquisition system, wherein the transformer is provided between the data acquisition system and the transmission line segments for correcting an impedance mismatch between the slipring and the electrical connection.

In another exemplary embodiment of the invention, a method of connecting a data slipring having transmission line segments with a data acquisition system includes providing a controlled impedance electrical cable between the transmission line segments and the data acquisition system.

In another exemplary embodiment of the invention, a direct electrical connection between a data slipring and a data acquisition system includes a controlled impedance electrical cable having a first end and a second end, the first end connected to the data slipring and the second end connected to the data acquisition system.

In another exemplary embodiment of the invention, a direct electrical connection between a data slipring and a data acquisition system includes a controlled impedance electrical cable having a first end and a second end and a transformer positioned on the data slipring, wherein the first end of the cable is connected to the transformer and the second end is connected to the data acquisition system.

Other systems, methods, and/or computer program products according to embodiments will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF DRAWINGS

Referring to the exemplary drawings wherein like elements are numbered alike in the several FIGS..

DETAILED DESCRIPTION

Figure 2:
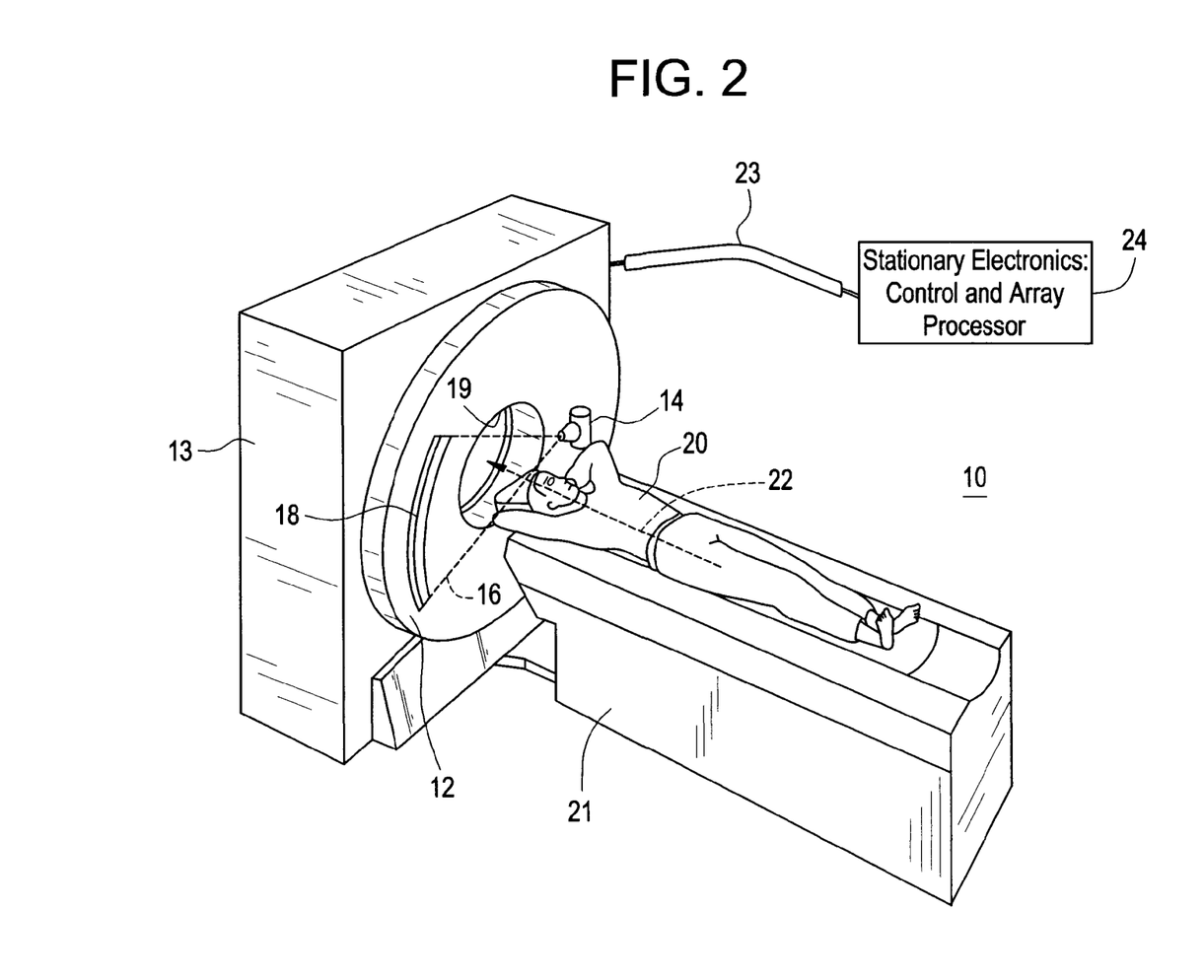
FIG. 2 shows a perspective view of a CT system which employs the present invention.

Referring to FIG. 2, a computerized tomography ("CT") system 10 includes a generally annular rotating frame 12 or gantry, and a stationary frame 13 that supports rotating frame 12. Rotating frame 12 includes an x-ray source 14 for emitting a highly collimated x-ray beam 16 toward a detector array 18 positioned on the opposite side of an aperture 19. Aperture 19 permits a test object 20, such as a patient, to be placed on a platform 21 which may be movable, for example, by translation, along rotating frame's 12 rotational axis 22. Movement of platform 21 allows different cross-sectional portions of interest of test object 20 to be positioned within the imaging plane of rotating frame 12.

Once test object 20 has been positioned within aperture 19, as desired, by movement of test object 20 and/or platform 21, rotating frame 12 rotates about the rotational axis 22, and at each of a plurality of angular positions along the rotational path, x-ray source 14 emits x-ray beam 16 which passes through test object 20 and is incident on the receiving surfaces of a plurality of detector elements (not individually shown) of the detector array 18. In response, each of the detector elements of detector array 18 produces an electrical signal at a magnitude proportional to the intensity of the received rays, and thus to the amount of attenuation of the x-ray beam after passing through test object 20. The signals from each of the detector elements of detector array 16, which represent the projection data, are presented through lines 23 to a control and array processor 24 that processes the received projection data into a radial image of test object 20 at the selected radial or angular position, which is referred to as a view. Then the aggregate of the views taken over a full revolution of the rotating frame 12, generally referred to as a scan, are further processed, using known image processing algorithms, into a cross-sectional image of the portion of interest of test object 10 that was within the imaging plane.

Figure 3:
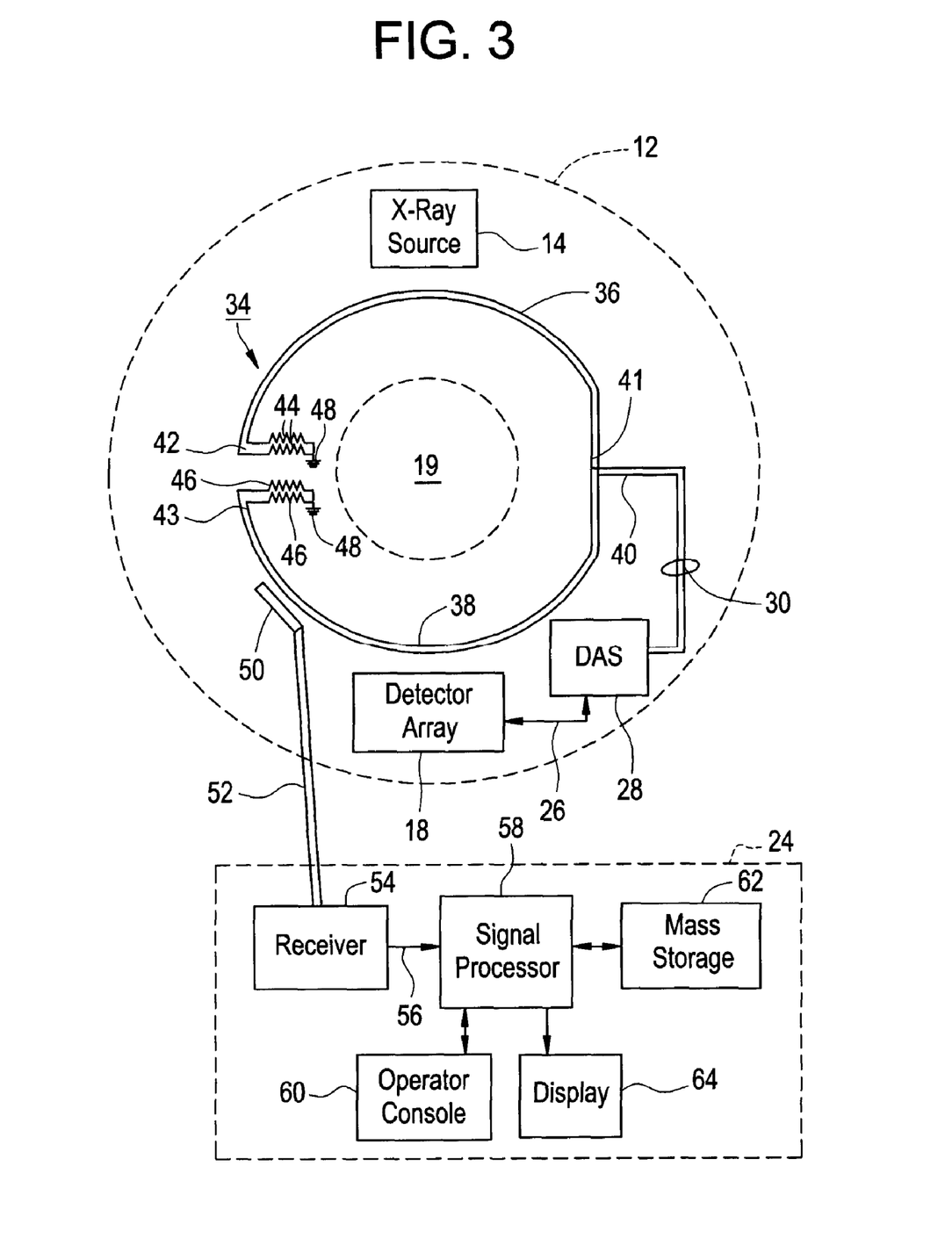
FIG. 3 shows a schematic block diagram of portions of the CT system of FIG. 2.

Referring now to FIG. 3, there is shown a schematic block diagram of a portion of the CT system 10 of FIG. 2. It should be understood that only functional elements necessary for a teaching of the present invention are shown in FIG. 2 and that only the relative connections between functional elements are shown. The signals from the detector array 18 are provided through lines 26 to a data acquisition system ("DAS") 28 disposed on rotating frame 12, which converts each signal from a detector element of detector array 18 from an analog signal format into a digital binary signal format, typically a 16 bit digital value representing the attenuated x-ray intensity. DAS 28 multiplexes the converted detector channel signals, together with a data clock signal and an error checking signal function, into a serial digital bit signal. The serial digital bit signal is then received by a transmitter 32, disposed on rotating frame 12, via lines 30. As will be further described, the DAS 28 may be directly connected to transmission line segments 36, 38 of an RF slipring 34 via a cable 30 to present the data signal.

The encoded data signal is propagated along transmission line segments 36, 38 to be electromagnetically coupled into a coupler 50 disposed on the stationary frame 13. RF slipring 34 may be configured to include one or more transmission lines disposed on rotating frame 12. Depending on the distance, generally referred to as the air gap, between the coupler 50 and the transmission line segments 36, 38, more transmission line segments may be required to ensure that coupler 50 is in sufficient spatial proximity to at least one of the transmission line segments to receive the encoded data signal. When more than one segment is required, each segment may have a length that is a fractional portion of the arc length of the rotating frame's 12 rotational path. The segments may be cascaded, end-to-end around the rotating frame's 12 rotational axis 22 (see FIG. 2), typically along the circumference of aperture 19, such that the aggregate segment length provides a substantially 360 degree arc, e.g., fully encircling the rotating frame 12.

Two transmission line segments 36, 38 having first ends 40, 41 and second ends 42, 43, respectively, may be contiguously positioned on rotating frame 12 encircling aperture 19 such that substantial continuity of electromagnetic coupling along the full rotational path of rotating frame 12 is possible. The first ends 40, 41 are connected to the cable 30, and the second ends 42, 43 are connected through terminal impedances 44, 46, respectively, to an electrical ground 48. The terminal impedances 44, 46 have a predetermined resistance value chosen to minimize reflection of energy in each of the transmission line segments 36, 38. Impedance matching will be further described below.

The coupler 50 may be positioned on the stationary frame 13 such that physical proximity between coupler 50 and at least one of the transmission line segments 36, 38 will be maintained during rotation of rotating frame 12. The air gap between coupler 50 and the transmission lines 36, 38 of slipring 34 may be in the range of approximately 0.050 to 0.080 inches, and coupler 50 may be a short piece of wire or transmission line approximately 2 inches in length. Coupler 50 may alternately be a pickup antenna, a RF shoe, a contactless brush, or an electromagnetic coupling apparatus capable of receiving the encoded data signal from the RF slipring 34 across a transmitting distance in the range of approximately 0.050 to 0.080 inches.

The cable 30 may deliver the encoded data signal to the first ends 40, 41 of the transmission lines 36, 38, respectively, and the encoded data signal propagates from the first ends 40, 41 to the second ends 42, 43 to be terminated at the electrical ground 48. Before the encoded data signal propagates to ground 48, however, the encoded data signal may be electromagnetically coupled to coupler 50, thereby completing the transfer from the rotating frame 12 to the stationary frame 13 for signal processing.

On the stationary frame side, the coupled encoded data signal, also referred to as the coupled modulated data signal, may be transmitted to a receiver 54 located in the control and array processor 24 via lines 52. The lines 52 may remain fiber optic because of the length involved for this datapath. The receiver 54 may decode the coupled modulated data signal to its pre-encoded state and provide this decoded signal to a signal processor 58 via lines 56. The signal processor 58 includes a computer and signal memory for storing the program algorithms which govern the CT processing of the received data in response to operator commands and scanning parameters received via an operator console 60, such as a keyboard, mouse, trackball, or switches. Although not shown, the operator commands and parameters are used by the signal processor 58 to provide control signals and information to the DAS 28, the x-ray controller (not shown), the gantry motor controller (not shown), as well as controlling movement of platform 21. In this manner, the signal processor 58 collates the decoded signal, i.e. the projection data, into a composite view corresponding to a particular angular position of the rotating frame 12. Each composite view is stored in a mass storage device 62 and is retrieved as necessary during processing of other composite views to be further processed to provide a final image of the desired cross-section of test object 20. This final image, also referred to as a reconstructed image, can then be displayed on a display 64, for example as a convention cathode ray tube ("CRT") display, a liquid crystal display, or other display devices, or it may be converted to a film or printed record by means of an appropriate computer controlled camera or printer (not shown). Moreover, reconstructed images may be stored in the mass storage 62 and stored reconstructed images and/or other data may be retrieved as commanded by the operator via the operator console 60 and the signal processor 58.

Figure 4:
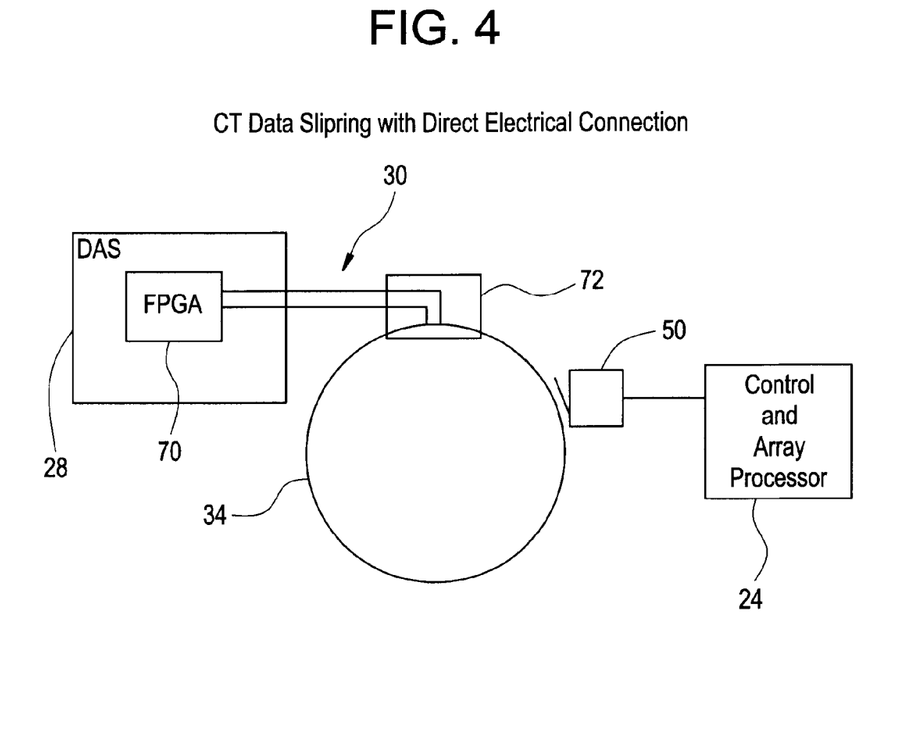
FIG. 4 shows a schematic block diagram of portions of the CT system of FIG. 2.

FIG. 4 shows a simplified schematic of a portion of the CT system 10 including the DAS 28, slipring 34, coupler 50, and control and array processor 24. The DAS 28 may include a field programmable gate array ("FPGA") 70, which is an integrated circuit that contains many identical logic cells that can independently take on any one of a limited set of personalities which are interconnected by a matrix of wires and programmable switches. The DAS 28 may alternately include a complex programmable logic device ("CPLD") or other related device. The cable 30 extends from the FPGA 70 in the DAS 28 and may directly connect to the slipring 34 at connection 72.

Figure 5:
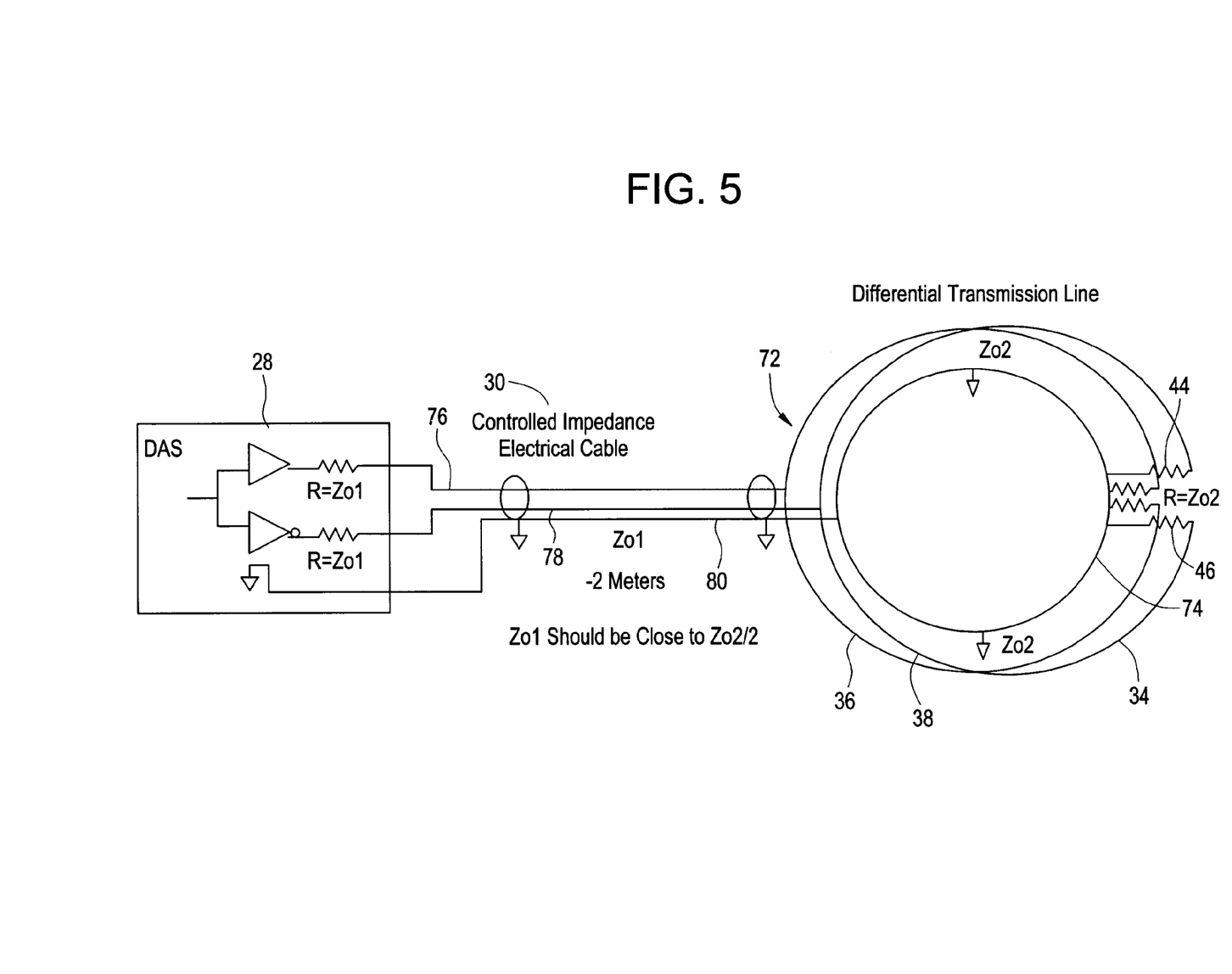
FIG. 5 shows a schematic block diagram of portions of the CT system of FIG. 2.

FIG. 5 shows a more detailed view of the direct connection 72 where the cable 30, such as a controlled impedance electrical cable, connects to the slipring 34 at connection 72. The cable 30 may include a plurality of wires including a first wire 76 extending from the DAS 28 to the slipring 34, and attached to the slipring 34 at transmission line segment 36. A second wire 78 may extend from the DAS 28 to the slipring 34, and attach to the slipring 34 at transmission line segment 38. A third wire 80 may extend from the DAS 28 to the slipring 34, connecting a line segment 74 to ground. The ground may really be a high-frequency return path in case there is the presence of common-mode signals. This may be the shield of the wire conductor. While this may be able to be eliminated in some cases, because of its effectiveness at limiting EMC and RF radiation, it should be included. It should also be noted that the number of wires is exemplary, and that the cable 30 may include more wires as is necessary to provide adequate connections to the slipring 34. It should further be noted that the direct connection 72 with controlled impedance electrical cable 30 allows elimination of the transmitter 108 with fiber optic receiver 106 and power supply 112 and the fiber optic transmitter 102 in DAS 28.

As further shown in FIG. 5, the resistance over the resistors in the DAS 28 for the first wire 76 and the second wire 78 may equal $Zo1$, while the resistance over the resistors 44 and 46 which connect the second ends 42, 43 of the transmission line segments 36, 38 may equal $Zo2$. For an impedance mismatch which is not great enough to cause undesired reflections and common mode noise which does not affect the signal integrity, $Zo1$ should be as close as possible to $Zo2/2$.

If the wires are not controlled impedance, then the electronic drivers in DAS 28 would have to be put close (within inches) of the transmission lines 36, 38 in order to not have signal reflections. The controlled impedance cable 30, however, allows the DAS 28 to be a manageable distance (such as, for example, a few meters) from the transmission line connection point.

As further shown in FIG. 5, the wires 76, 78 in cable 30 have a controlled characteristic impedance of $Zo1$ with respect to the ground wire 80. The termination resistors in DAS 28 have a resistance value equal or close to $Zo1$ to minimize electrical reflections. The transmission lines 36 and 38, have a characteristic impedance of $Zo2$ with respect to ground 74 and have termination resistors 44, 46 that have a resistance value equal or close to $Zo2$. The wires 76 and 78 are connected to transmission lines 36 and 38, respectively. If $Zo1$ is not equal to $Zo2/2$, then there is a mismatch in impedances and electrical reflections will degrade the waveform fidelity. However, if the impedances $Zo1$ and $Zo2/2$ are close enough (for example, $(0.2)Zo1 < Zo2/2 < (5) Zo1$), then the waveform fidelity may be acceptable. Using a numeric example, if $Zo1=50$ ohms and $Zo2=40$ ohms, then 10 ohms$<20$ ohms$<250$ ohms. Thus, satisfying the rule $(0.2)Zo1 < Zo2/2 < (5) Zo1$ may provide for acceptable waveform fidelity. As will be discussed further below, the impedance matching range used for FIGS. 4–5 is for a system which does not incorporate a transformer.

One example of a cable 30 which is able to control impedance in the connection between the DAS 28 and the slipring 34 is a high speed copper cable, and its associated connectors, which reduce the crosstalk and noise that was a problem with copper assemblies of the past. One such high speed copper cable is the commercially available InfiniBand copper cable, such as the InfiniBand copper cables and adapters available from Sierra Technologies, LLC, although other suppliers of the InfiniBand copper cables would be within the scope of this invention. The InfiniBand technology, previously called "System I/O" is a result of the merger of two competing designs, Future I/O, which was developed by Compaq, IBM, and Hewlett-Packard, and Next Generation I/O, which was developed by Intel, Microsoft and Sun Microsystems. Instead of sending data in parallel, as a PCI bus does, InfiniBand sends data in serial and can carry multiple channels of data at the same time in a multiplexing signal.

Figure 6:
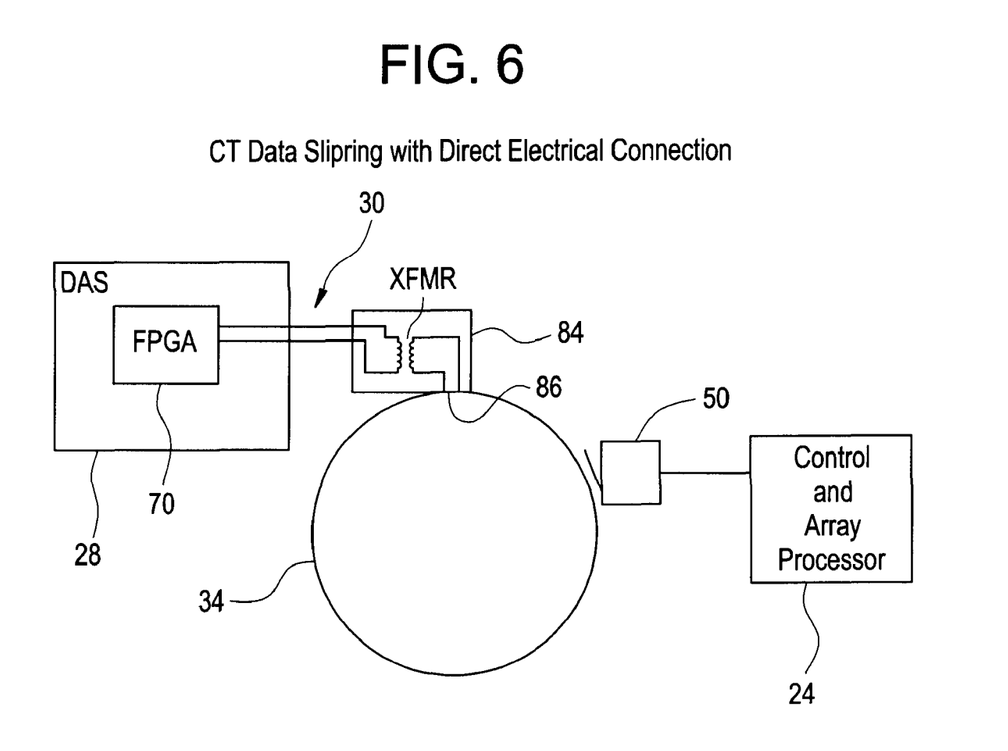
FIG. 6 shows a schematic block diagram of another embodiment of portions of the CT system of FIG. 2; and, FIG. 7 shows a schematic block diagram of another embodiment of portions of the CT system of FIG. 2.
Figure 7:
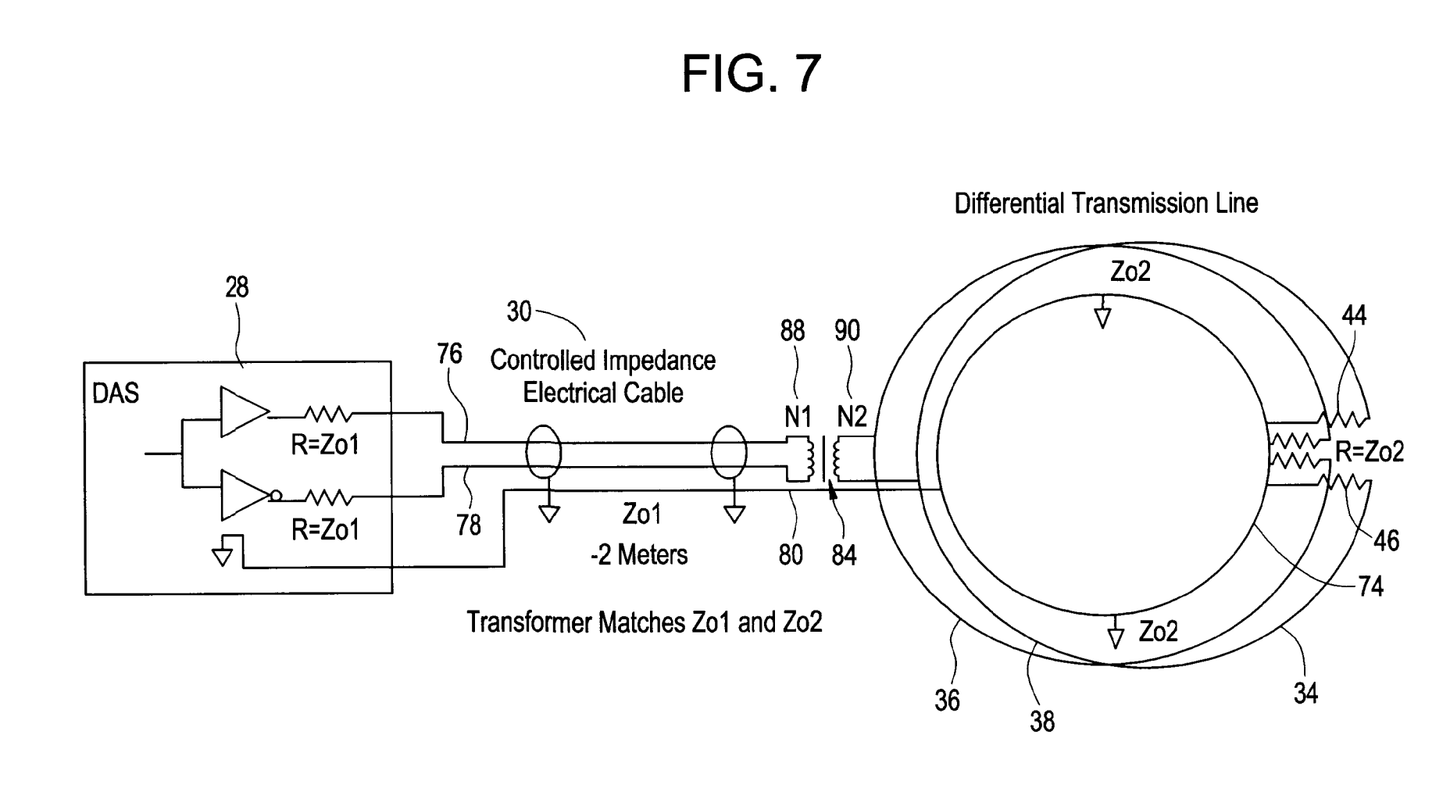

As previously discussed, the impedance mismatch should be as small as possible for preventing undesired reflections and common mode noise which may affect signal integrity. Turning now to FIGS. 6–7, another embodiment of the system 10 is shown, for when the impedance mismatch is too great for the intended application. The impedance mismatch may be too great, for example, when the relationship $(0.2)Zo1 < Zo2/2 < (5) Zo1$ is not true. A transformer 84 may be added at the connection point 86 between the controlled impedance electrical cable 30 and the slipring 34. The transformer is positioned between the controlled impedance cable 30 and the slipring transmission lines 36, 38 to correct the mismatch so that the reflections will be minimized. It should be understood however, that, if desired, a transformer 84 may be added to the system 10 even if the relationship $(0.2)Zo1 < Zo2/2 < (5) Zo1$ is true. The transformer 84 is preferably a low cost high speed transformer for eliminating the common mode noise and reducing reflections due to any impedance mismatch. Thus, the high speed slipring signal, which may originate at the RF pickup, may pass through the transformer 84, which reduces reflections by matching the impedance difference between the slipring 34 and that of the cable 30 and eliminates common mode noise, going straight to the DAS 28 without the need for an optical to electrical conversion.

It should be understood that the transformer 84 may include two windings which may convert one AC voltage to another AC voltage. A first voltage passes through a primary winding, which may be wound around a metallic or iron core. The AC current in the primary winding may create an alternating magnetic field in the core just as it would in an electromagnet. A secondary winding may wrap about the same core and the magnetic field in the core may create current. The voltage in the secondary winding may be controlled by the ratio of the number of turns in the two windings. For example, if the primary and secondary windings have the same number of turns, the primary and secondary voltage would be the same. Also by way of example, if the secondary winding has half as many turns as the primary winding, then the voltage in the secondary winding may be half that of the voltage in the primary winding.

With further reference to FIGS. 6–7, the transformer turns ratio may be selected to eliminate mismatch or match impedances as closely as possible. As shown in FIG. 7, where the turns of the transformer 84 are represented diagrammatically as N1 88 and N2 90, $(N1/N2)^2$ should be chosen to be as close as possible to $Zo1/(Zo2/2)$. As a numeric example, if $Zo1=50$ and $Zo2=40$, then the turns ratio $N1/N2$ should be approximately equal to, or equal to 1.6. Thus, when the resistances $Zo1$ and $Zo2$ are determined, and if it is determined that the impedance mismatch in the system is too great, for example if $(0.2)Zo1 < Zo2/2 < (5) Zo1$ is not true, then an appropriate transformer 84 can be selected which has a turns ratio $N1/N2$ which is equivalent to a square root of $Zo1/(Zo2/2)$.

While fiber optics have numerous benefits, copper cabling is also advantageous as it has high electric conductivity, and is energy efficient, strong, ductile, and does not react with modern insulation materials. By using high speed copper cable technology, expensive optical transmission equipment and associated electronics are not necessary thus reducing the cost of the CT system. The cost savings realized may be approximately between $1,000 to $2,000. Also, advantageously, the overall complexity of the transmission circuit is reduced thereby removing a number of possible failure points and increasing reliability and serviceability.

While the invention has been described with reference to exemplary embodiments, it will be understood by those skilled in the art that various changes may be made and equivalents may be substituted for elements thereof without departing from the scope of the invention. For example, the system may be applicable to a nuclear medicine imaging system, or other types of modalities not specifically described herein. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A system for image reconstruction comprising:
   a data slipring including transmission line segments;
   a data acquisition system; and,
   a direct electrical connection between the transmission line segments and the data acquisition system;
   wherein the direct electrical connection includes a first wire connecting a first resistor in the data acquisition system to a first transmission line segment and a second wire connecting a second resistor in the data acquisition system to a second transmission line segment;
   wherein the first and second resistors have a resistance $Zo1$, and wherein first ends of the first and second transmission line segments are connected to the first and second wires, respectively, and wherein second ends of the first and second transmission line segments are connected to resistors having a resistance $Zo2$, wherein a difference between $Zo1$ and $Zo2/2$ is minimized.

2. The system of claim 1 comprising a controlled impedance electrical cable for providing the direct electrical connection.

3. The system of claim 1 comprising a high speed copper cable for providing the direct electrical connection.

4. The system of claim 3 wherein the high speed copper cable sends data in serial.

5. The system of claim 3 wherein the high speed copper cable is an InfiniBand copper cable.

6. The system of claim 1 wherein the direct electrical connection extends from a field programmable gate array to the transmission line segments.

7. The system of claim 1 wherein the direct electrical connection includes a third wire connecting to ground.

8. The system of claim 1 wherein $(0.2)Zo1 < Zo2/2 < (5) Zo1$.

9. The system of claim 1 wherein when $(0.2)Zo1 < Zo2/2 < (5)Zo1$ is not true, where $Zo1$ is a resistance over resistors connecting the data acquisition system to wires in the direct electrical connection and $Zo2$ is a resistance between ends of the transmission line segments, the system further comprises a transformer connected between the transmission line segments and the direct electrical connection.

10. The system of claim 1 wherein the system is a computed tomography system.

11. A system for image reconstruction comprising:
    a data slipring including transmission line segments;
    a data acquisition system;
    a transformer and,
    an electrical connection between the transmission line segments and the data acquisition system, wherein the transformer is provided between the data acquisition system and the transmission line segments for correcting an impedance mismatch between the slipring and the electrical connection;
    wherein a turns ratio of the transformer is equivalent to a square root of $Zo1/(Zo2/2)$ where $Zo1$ is a resistance over resistors connecting the data acquisition system to wires in the electrical connection and $Zo2$ is a resistance between ends of the transmission line segments.

12. The system of claim 11 comprising a controlled impedance electrical cable for providing the electrical connection.

13. The system of claim 11 comprising a high speed copper cable for providing the electrical connection.

14. The system of claim 13 wherein the high speed copper cable sends data in serial.

15. The system of claim 13 wherein the high speed copper cable is an InfiniBand copper cable.

16. A method of connecting a data slipring having transmission line segments with a data acquisition system, the method comprising:
provide a controlled impedance electrical cable between the transmission line segments and the data acquisition system; and
minimizing a difference between a resistance Zo1 in the data acquisition system and Zo2/2, where Zo2 is a resistance between ends of first and second transmission line segments.

17. The method of claim 16 wherein the controlled impedance electrical cable is a high speed copper cable.

18. The method of claim 16 wherein the cable provides an uninterrupted connection between the transmission line segments and the data acquisition system.

19. The method of claim 16 further comprising providing a transformer between the transmission line segments and the data acquisition system for correcting an impedance mismatch between the slipring and the cable.

20. The method of claim 19 further comprising connecting the transformer between the transmission line segments and the cable.

21. The method of claim 19 wherein a turns ratio of the transformer is equivalent to a square root of Zo1/(Zo2/2), where Zo1 is a resistance over resistors connecting the data acquisition system to wires in the cable and Zo2 is a resistance between ends of the transmission line segments.

22. The method of claim 16 wherein (0.2)Zo1<Zo2/2<(5)Zo1.

23. The method of claim 16 wherein, if (0.2)Zo1<Zo2/2<(5)Zo1 is true, where Zo1 is a resistance over resistors connecting the data acquisition system to wires in the cable and Zo2 is a resistance between ends of the transmission line segments, then providing an uninterrupted connection between the transmission line segments and the data acquisition system, and if (0.2)Zo1<Zo2/2<(5)Zo1 is not true, then providing a transformer between the transmission line segments and the cable.

24. A direct, non-optical, electrical connection between a data slipring and a data acquisition system, the direct electrical connection comprising:
a controlled impedance electrical cable having a first end and a second end, the first end connected to the data slipring and the second end connected to the data acquisition system;
wherein (0.2)Zo1<Zo2/2<(5)Zo1, where Zo1 is a resistance over resistors connecting the data acquisition system to wires in the cable and Zo2 is a resistance between ends of transmission line segments in the data slipring.

25. The connection of claim 24 wherein the cable is a high speed copper cable.

26. The connection of claim 25 wherein the high speed copper cable is an InfiniBand copper cable.

27. A direct, non-optical, electrical connection between a data slipring and a data acquisition system, the direct electrical connection comprising:
a controlled impedance electrical cable having a first end and a second end; and,
a transformer positioned on the data slipring, wherein the first end of the cable is connected to the transformer and the second end is connected to the data acquisition system;
wherein a turns ratio of the transformer is equivalent to a square root of Zo1/(Zo2/2), where Zo1 is a resistance over resistors connecting the data acquisition system to wires in the cable and Zo2 is a resistance between ends of transmission line segments in the data slipring.

28. The connection of claim 27 wherein the cable is a high speed copper cable.

29. The connection of claim 28 wherein the high speed copper cable is an InfiniBand copper cable.

* * * * *